US006025829A

United States Patent [19]
DeLucia et al.

[11] Patent Number: 6,025,829
[45] Date of Patent: *Feb. 15, 2000

[54] IMAGE GENERATOR FOR VIDEO DISPLAY

[75] Inventors: Paul DeLucia, Baldwinsville; Arthur G. Avedisian; Jon R. Salvati, both of Skaneateles, all of N.Y.

[73] Assignee: Welch Allyn, Inc., Skaneateles Falls, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/736,826

[22] Filed: Oct. 28, 1996

[51] Int. Cl.[7] ........................................................ G09G 5/10

[52] U.S. Cl. .......................... 345/149; 345/153; 345/432; 345/515

[58] Field of Search ........................................ 345/112, 132, 345/133, 147, 148, 149, 501, 432, 507, 515, 25, 114, 471, 443, 425, 145; 382/159; 351/246, 239; 348/136

[56] References Cited

U.S. PATENT DOCUMENTS

| | | |
|---|---|---|
| 3,422,419 | 1/1969 | Matthews et al. . |
| 3,571,807 | 3/1971 | Candy ...................................... 345/508 |
| 3,659,285 | 4/1972 | Baer et al. ............................... 345/157 |
| 3,750,133 | 7/1973 | Helbig, Sr. et al. ....................... 345/25 |
| 3,793,483 | 2/1974 | Bushnell ................................. 345/121 |
| 3,821,468 | 6/1974 | Busch . |
| 3,836,902 | 9/1974 | Okuda et al. ............................ 345/509 |
| 3,874,669 | 4/1975 | Ariano et al. ............................ 345/473 |
| 3,883,235 | 5/1975 | Lynn et al. ............................... 351/246 |
| 3,936,664 | 2/1976 | Sato .......................................... 345/17 |
| 4,026,555 | 5/1977 | Kirschner et al. ....................... 345/168 |

(List continued on next page.)

FOREIGN PATENT DOCUMENTS

| | | |
|---|---|---|
| 85182863 | 3/1983 | Russian Federation . |
| 94/05202 | 3/1994 | WIPO . |
| 95/29627 | 9/1995 | WIPO . |
| WO 95/29627 | 11/1995 | WIPO . |

OTHER PUBLICATIONS

A Versatile Video Pattern Generator for Vision Test,Proceedings of the International Phoenix Conference on Computers and Communications, Tempe, Arizona—pp. 545–551 Mar. 23–26, 1993, IEEE.

Alpex Computer Corp. v. Nintendo Co. Ltd., 40 USPQ2d 1667 (CAFC 1996).

The Journal of Physiology, Jan. 1, 1995, vol. 482.1, pp. 189–203, Vo Van Toi and C.E. Riva.

Precision Machinery, 1987, vol. 1, pp. 355–376, Vo Van Toi, C.W. Burckhardt and P.A. Grounauer.

Optics Letters, Sep. 1, 1989, vol. 14, No. 17, pp. 907–909, Vo Van Toi.

Noninvasive Assessment of the Visual System Technical Digest, 1992 (Optical Society of America, Washington, D.C. 1992), vol. 1, pp. 198–201.

Applied Optics, Jun. 1, 1991, vol. 30, No. 16, pp. 2113–2120, Vo Van Toi, C. W. Burckhardt, and P. A. Grounauer.

*Primary Examiner*—Chanh Nguyen
*Assistant Examiner*—John Suraci
*Attorney, Agent, or Firm*—Wall Marjama Bilinski & Burr

[57] ABSTRACT

An image generator generates brightness modulated bars for a video monitor. The bars run parallel to the scan line of the monitor allowing the use of a relatively slow digital to analog converter (DAC). A frame buffer need only be as deep as a number of different shades desired on a particular scan line, instead of needing to be as deep as the resolution of the DAC. Using a multiplexer allows use of a 1 bit deep frame buffer instead of a conventional 12 bit deep frame buffer. A feature of the image generator allows efficient determination of a mean gray scale used in generating the brightness modulated bars. The brightness modulation scheme is sinusoidal, that is, based on a sine function, for specified applications but can be any other modulation scheme based on, for example, a sawtooth function, a step function, an exponential function, and so forth.

16 Claims, 6 Drawing Sheets

U.S. PATENT DOCUMENTS

| | | | |
|---|---|---|---|
| 4,155,352 | 5/1979 | Toglia et al. | 600/546 |
| 4,251,755 | 2/1981 | Bryden | 345/147 |
| 4,297,691 | 10/1981 | Kodama et al. | 345/147 |
| 4,493,539 | 1/1985 | Cannon, Jr. | 351/205 |
| 4,526,452 | 7/1985 | Hirsh | 351/243 |
| 4,541,115 | 9/1985 | Werth | 382/159 |
| 4,604,555 | 8/1986 | Karaki | 345/147 |
| 4,607,923 | 8/1986 | Task et al. | 351/239 |
| 4,623,923 | 11/1986 | Orbach | 348/625 |
| 4,642,676 | 2/1987 | Weinger | 348/578 |
| 4,676,611 | 6/1987 | Nelson et al. | 351/205 |
| 4,704,605 | 11/1987 | Edelson | 345/153 |
| 4,779,223 | 10/1988 | Asai et al. | 345/59 |
| 4,910,681 | 3/1990 | Ohtake et al. | 348/181 |
| 4,977,398 | 12/1990 | Pleva et al. | 345/147 |
| 5,001,549 | 3/1991 | Holmbo et al. | 348/182 |
| 5,065,767 | 11/1991 | Maddess | 351/239 |
| 5,170,468 | 12/1992 | Shah et al. | 345/501 |
| 5,176,147 | 1/1993 | Bodis-Wollner | 351/239 |
| 5,233,517 | 8/1993 | Jindra | 356/223 |
| 5,248,964 | 9/1993 | Edgard et al. | 345/25 |
| 5,270,688 | 12/1993 | Dawson et al. | 345/147 |
| 5,270,815 | 12/1993 | Okumura et al. | 348/497 |
| 5,303,709 | 4/1994 | Dreher et al. | 351/206 |
| 5,319,446 | 6/1994 | Emmoto et al. | 348/181 |
| 5,337,408 | 8/1994 | Fung et al. | 345/149 |
| 5,360,971 | 11/1994 | Kaufman et al. | 250/221 |
| 5,479,606 | 12/1995 | Gray | 345/149 |
| 5,491,496 | 2/1996 | Tomiyasu | 345/186 |
| 5,539,482 | 7/1996 | James et al. | 351/246 |
| 5,543,819 | 8/1996 | Farwell et al. | 345/147 |
| 5,600,773 | 2/1997 | Vanover et al. | 345/149 |
| 5,636,335 | 6/1997 | Robertson et al. | 345/431 |

Q1_S2

Q1_S1

Q1_S3

Q1_S4

Q4_S2

Q4_S1

Q4_S3

Q4_S4

Q2_S2

Q2_S1

Q2_S3

Q2_S4

Q3_S2

Q3_S1

Q3_S3

Q3_S4

IMAGE GENERATOR FOR VIDEO DISPLAY

BACKGROUND OF THE INVENTION

This invention relates to an image generator for a video display, and in particular, to an image generator for generating accurate graphical images for a video monitor.

There are several medical diagnostic and research instruments that require sinusoidal gratings on an illuminated screen. For example, a method for testing for glaucoma known as frequency doubled perimetry involves having a patient observe a sinusoidal grating pattern in a number of different regions of a display screen of a video monitor. The contrast of the pattern is varied until the patient observing the well known phenomenon of visual frequency doubling notes the cessation of the phenomenon, thereby establishing a contrast sensitivity for that patient. The contrast sensitivity is compared to the contrast sensitivity for persons of normal vision. A significant deviation from the norm in contrast sensitivity may indicate some degradation of the visual function, possibly due to the presence of glaucoma, AMD (age related macular degeneration), diabetic retinopathy, or other disease. Some testing methods are presented in detail in U.S. Pat. Nos. 5,295,495 and 5,065,767 incorporated herein by reference.

Producing the required contrast bars, or grating, requires providing video timing signals and a high resolution gray scale video signal to the video monitor. A conventional approach to generating a video signal of the necessary high resolution includes using a video coprocessor, a 12 bit deep frame buffer, and a very fast bit digital to analog converter (DAC). There are several disadvantages to this conventional approach.

First, nearly 420 KBytes of fast VRAM are required for the frame buffer. Updating such a frame buffer with a new screen pattern in 10 msec., necessary for each contrast adjustment to appear instantaneous to the viewer, requires a data bus bandwidth of 2.6 Mwords/sec (1 word equals 12 bits) along with a DAC that is fast enough to handle the data bus speed.

Second, the expense of currently available high integration video controller IC's capable of such graphics, a very fast DAC, and a 12 bit deep frame buffer add significantly to the overall cost of a conventional video generator adapted to this special use.

OBJECTS AND SUMMARY OF THE INVENTION

It is therefore an object of the present invention to provide an inexpensive image generator with high quality and accuracy.

Another object of the present invention is to provide an image generator especially suited for use in testing the human visual system.

Still another object of the invention is to provide an image generator for producing a graphic image.

A further object of the invention is to provide an image generator for producing a graphic image that is brightness modulated.

A still further object of the present invention is to provide an image generator capable of producing a sinusoidal grating.

Briefly stated, an image generator generates brightness modulated bars for a video monitor. The bars run parallel to the scan line of the monitor allowing the use of a relatively slow digital to analog converter (DAC). A frame buffer need only be as deep as a number of different shades desired on a particular scan line, instead of needing to be as deep as the resolution of the DAC. Using a multiplexer allows use of a 1 bit deep frame buffer instead of a conventional 12 bit deep frame buffer. A feature of the image generator allows efficient determination of a mean gray scale used in generating the brightness modulated bars. The brightness modulation scheme is sinusoidal, that is, based on a sine function, for specified applications but can be any other modulation scheme based on, for example, a sawtooth function, a step function, an exponential function, and so forth.

According to an embodiment of the invention, an image generator for a video monitor includes processing means for processing data, the processing means including means for storing a pattern, generating means, responsive to the processing means, for generating an analog shade signal from an output of the processing means, means for generating an analog mask signal, and selecting means, responsive to the pattern, for alternately selecting one of the shade signal and the mask signal to produce a selected signal, the selected signal being effective as a single scan line video input to the video monitor.

According to an embodiment of the invention, an image generator includes a microcontroller outputting a digital shade signal, a shade DAC receiving the digital shade signal as an input and outputting an analog shade signal, a mask voltage reference generating an analog mask signal, the microcontroller storing a pattern in a memory, the microcontroller outputting the pattern to a shift register, an analog MUX receiving the analog shade signal and the analog mask signal as inputs, and the analog MUX outputting one of the analog shade signal and the analog mask signal depending on an output received from the shift register.

According to an embodiment of the invention, an image generator for generating a grating of vertical bars for a video monitor includes processing means for processing data, the processing means including means for storing a pattern, shade generating means, responsive to the processing means, for generating an analog shade signal from an output of the processing means, means for generating an analog mask signal, selecting means, responsive to the processing means, for alternately selecting one of the shade signal and the mask signal to produce a selected signal, the selected signal being effective as a portion of a scan line of a video input to the video monitor to generate the grating, and a direction of the scan line being identical to a direction of the grating.

According to an embodiment of the invention, an image generator for generating a grating for a video monitor includes a microcontroller outputting a digital shade signal, a shade DAC receiving the digital shade signal as an input and outputting a first voltage level, means for generating a second voltage level, the microcontroller storing a pattern in a memory, the microcontroller outputting the pattern to a shift register, an analog MUX receiving the first and second voltage levels as inputs, and the analog MUX outputting a video input consisting of one of the first voltage level and the second voltage level depending on an output received from the shift register.

According to an embodiment of the invention, an image generator for generating a grating of brightness modulated bars for a video monitor includes an 1-bit deep frame buffer, an m-bit DAC for producing a first analog signal, means for generating a second analog signal of substantially level voltage, means, responsive to the frame buffer, for continuously selecting one of the first and second analog signals to produce a selected signal, a scan line input of the monitor consisting of the selected signal, wherein a brightness modulated bar of the grating is generated, and the brightness of the bar having a resolution of m-bits.

According to an embodiment of the invention, an image generator for generating a grating of brightness modulated bars for a video monitor includes means for generating an n-bit frame buffer signal, $2^n$ number of inputs, each of a given resolution, means for generating $2^n$ number of inputs, means responsive to the frame buffer for continuously selecting one of the $2^n$ inputs to produce a selected video signal, a brightness of a pixel having of the video signal having a resolution of the selected input.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

Figure 1A:
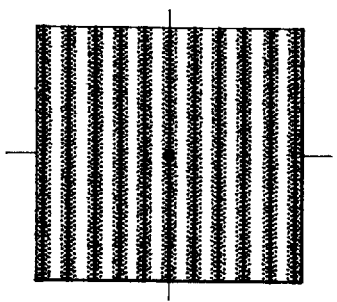
FIG. 1A shows a video monitor display screen with a vertical grating across the entire display screen.

Referring to FIG. 1A, a grating consisting of a series of vertical sinusoidally modulated bars is shown, although any modulated pattern can be used for the grating. Grating bars differ from solid bars in that solid bars consist of black and white stripes with a spatially instantaneous brightness transition when measured across the longitudinal, or X axis, whereas an intensity measured along the longitudinal axis of grating bars is a sinusoidal function of the X axis. The brightness (intensity) is constant along the transverse, or Y axis, for all values of Y at any fixed X coordinate.

Figure 1B:
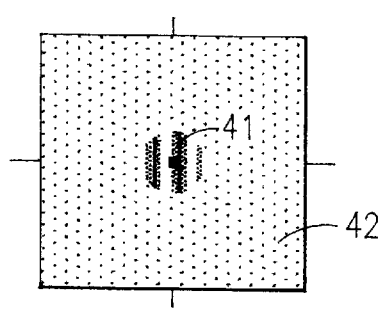
FIG. 1B shows a video monitor display screen with a vertical grating truncated by a 5 degree central aperture with a remainder of the display being a mean level of gray.
Figure 1C:
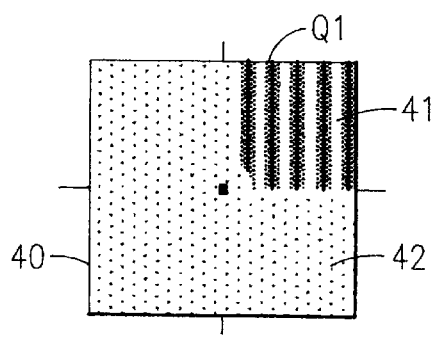
FIG. 1C shows a display screen with a vertical grating in a quadrant Q1 with a remainder of the display being a mean level of gray.
Figure 1D:
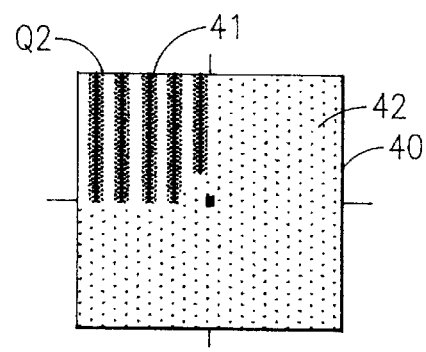
FIG. 1D shows a display screen with a vertical grating in a quadrant Q2 with a remainder of the display being a mean level of gray.
Figure 1E:
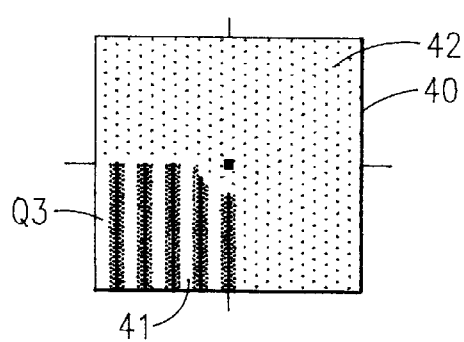
FIG. 1E shows a display screen with a vertical grating in a quadrant Q3 with a remainder of the display being a mean level of gray.
Figure 1F:
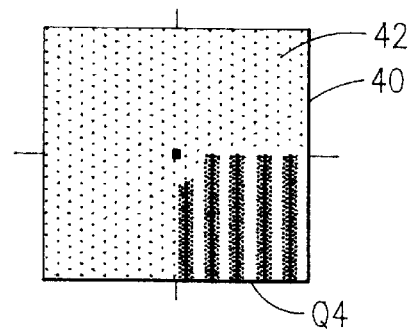
FIG. 1F shows a display screen with a vertical grating in a quadrant Q4 with a remainder of the display being a mean level of gray.
Figure 1H:
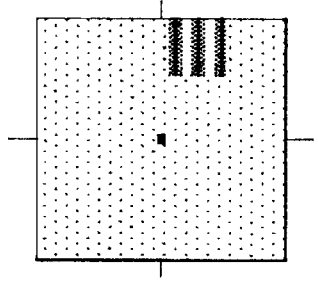
FIG. 1H shows a display screen with a vertical grating in a section S2 of quadrant Q1 with a remainder of the display being a mean level of gray.
Figure 2:
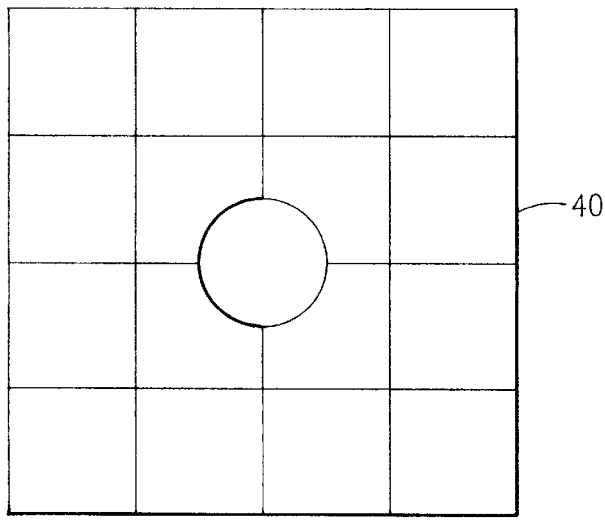
FIG. 2 shows a display screen divided into seventeen regions.

Referring to FIG. 2, a testing method known as frequency doubled perimetry includes dividing a display screen 40, preferably 40° by 40° in size, into 16 regions, preferably squares 10° by 10° in size. A 17th region is preferably a circle 5° in size centered within display screen 40 such as shown in FIG. 1B. An image portion 41 of display screen 40 contains the vertical grating. A remainder of display screen 40 is a mask portion 42. FIGS. 1C–1F show display screen 40 divided into quadrants Q1–Q4, respectively.

Figure 1G:
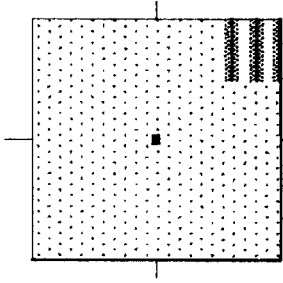
FIG. 1G shows a display screen with a vertical grating in a section S1 of quadrant Q1 with a remainder of the display being a mean level of gray.
Figure 1I:
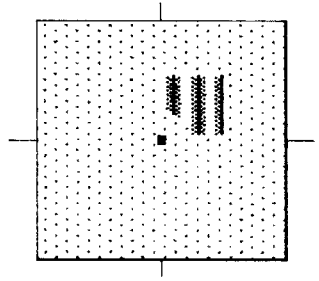
FIG. 1I shows a display screen with a vertical grating in a section S3 of quadrant Q1 with a remainder of the display being a mean level of gray.
Figure 1J:
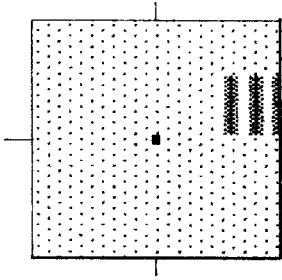
FIG. 1J shows a display screen with a vertical grating in a section S4 of quadrant Q1 with a remainder of the display being a mean level of gray.
Figure 1L:
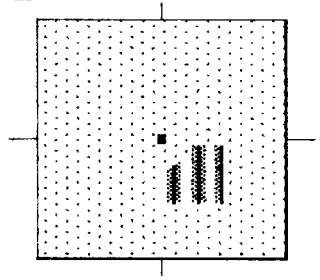
FIG. 1L shows a display screen with a vertical grating in a section S2 of quadrant Q4 with a remainder of the display being a mean level of gray.
Figure 1K:
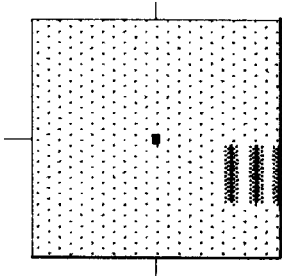
FIG. 1K shows a display screen with a vertical grating in a section S1 of quadrant Q4 with a remainder of the display being a mean level of gray.
Figure 1M:
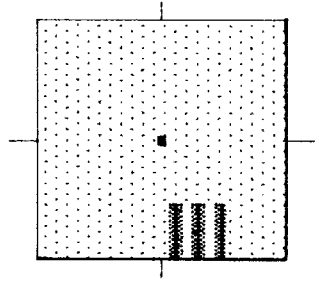
FIG. 1M shows a display screen with a vertical grating in a section S3 of quadrant Q4 with a remainder of the display being a mean level of gray.
Figure 1N:
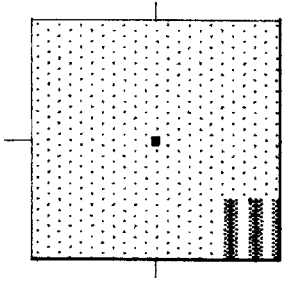
FIG. 1N shows a display screen with a vertical grating in a section S4 of quadrant Q4 with a remainder of the display being a mean level of gray.
Figure 1P:
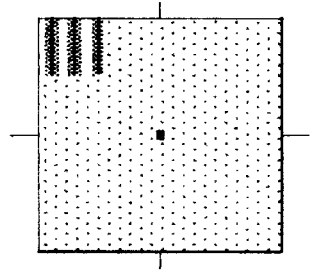
FIG. 1P shows a display screen with a vertical grating in a section S2 of quadrant Q2 with a remainder of the display being a mean level of gray.
Figure 1O:
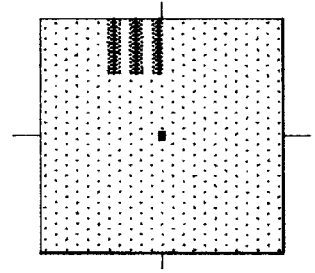
FIG. 1O shows a display screen with a vertical grating in a section S1 of quadrant Q2 with a remainder of the display being a mean level of gray.
Figure 1Q:
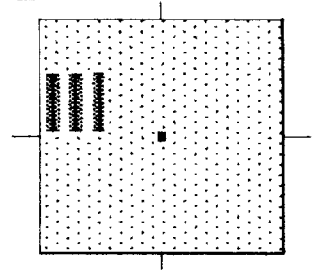
FIG. 1Q shows a display screen with a vertical grating in a section S3 of quadrant Q2 with a remainder of the display being a mean level of gray.
Figure 1R:
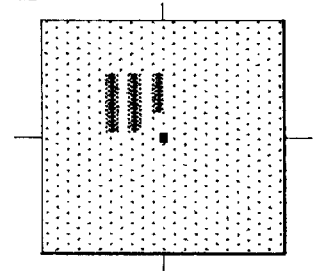
FIG. 1R shows a display screen with a vertical grating in a section S4 of quadrant Q2 with a remainder of the display being a mean level of gray.
Figure 1T:
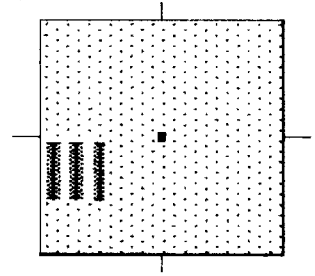
FIG. 1T shows a display screen with a vertical grating in a section S2 of quadrant Q3 with a remainder of the display being a mean level of gray.
Figure 1S:
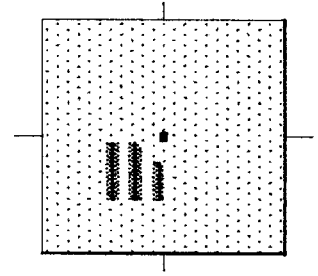
FIG. 1S shows a display screen with a vertical grating in a section S1 of quadrant Q3 with a remainder of the display being a mean level of gray.
Figure 1U:
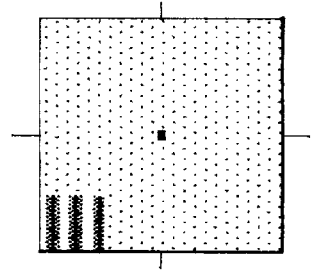
FIG. 1U shows a display screen with a vertical grating in a section S3 of quadrant Q3 with a remainder of the display being a mean level of gray.
Figure 1V:
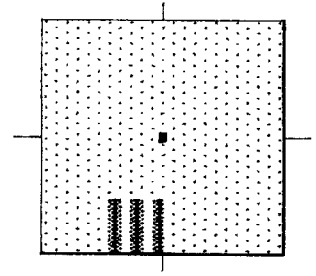
FIG. 1V shows a display screen with a vertical grating in a section S4 of quadrant Q3 with a remainder of the display being a mean level of gray.

FIGS. 1G–1V show a display screen with a vertical grating in regions Q1–S1 through Q4–S4. One of these regions is shown at a time to a patient with the grating (stimulus pattern) shown thereon. The pattern is then shifted 180° at a frequency, known as the temporal frequency, typically between 8 and 50 Hz, and preferably at 25 Hz. That is, during each temporal period, the brightest point (peak) of each grating sinusoid is cycled to become a trough (dimmest point) alternating every 20 msec. In effect, the display becomes its negative or is considered as shifting 180°.

The spatial frequency of the grating bars is typically between 0.2 to 2 cycles (of the sine wave) per degree (field of view).

The contrast of the waveform is adjusted during the test. Contrast is defined as the brightness ratio between the brightest (MAX) and dimmest (MIN) portions of the grating as shown by

C=(MAX−MIN)/(MAX+MIN)

with a value between 0 and 1. The grating sinusoids preferably are on a background of a mean level of gray. The light intensity along the X axis is shown by B=G(1+C*sin (X))

where B is the brightness at a point, G is the mean level of gray (also known as the DC component), C is the contrast as defined above, and sin(X) is the sine function of the X coordinate.

Different contrast levels are used during testing. For example, if the first contrast level used is 50% and the patient observes the doubling effect, the contrast level is lowered by a specified amount. If the patient does not observe the doubling effect at 50% contrast, the contrast level is raised by a specified amount. This step is repeated using an automated staircase procedure until a contrast threshold (contrast sensitivity) for that patient is determined. The contrast level is then compared to a mean contrast level of people with known normal vision to detect the presence of damage to the retina.

Different portions of the retina are tested by using square patterns presented in different areas of the visual field. Within the visual field, the order in which squares are presented is varied randomly to obtain reliable data from the patient.

Figure 3:
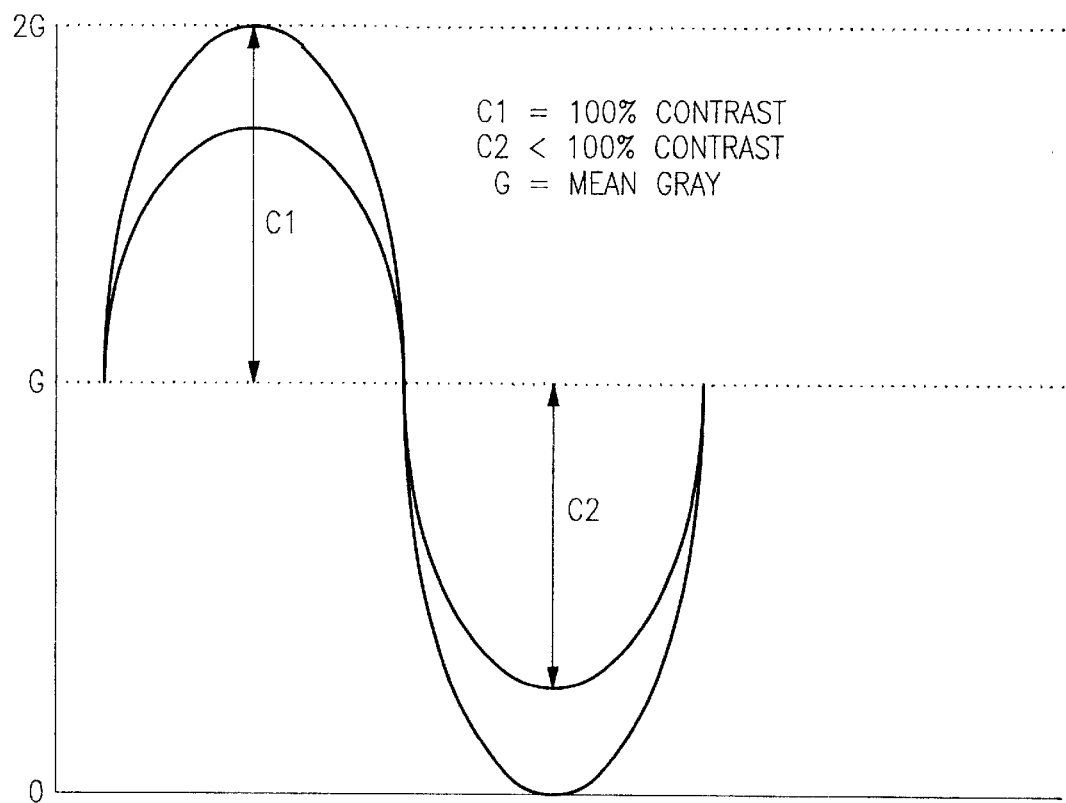
FIG. 3 is a graphical representation of a light intensity along the X axis.

Referring to FIG. 3, the function B=G(1+C*sin (X)) is shown graphically. The mean brightness must be kept constant during manipulation of the sinusoidally modulated gratings, such as, for example, during the inversion process and contrast adjustment. The regions of the screen that have no grating are masked to the mean gray level. A curve C1 depicts a contrast value of 100% while a curve C2 shows a contrast value less than 100%. Mean level of gray G is the midpoint on the Y axis. Note that at 100% contrast, the lowest value of the function is always zero brightness whereas the highest value of the function is 2G. As the contrast approaches zero, the brightness approaches mean level of gray G. That is, zero contrast gratings result in a full screen of mean level gray. This is also true for all points where X=0, 180, 360, 540, . . . degrees.

The actual graphical requirements of the gratings can be realized using simpler electronics than are used in conventional systems. If the horizontal scan lines are arranged on the transverse axis instead of the traditional longitudinal axis, the conventional 12 bit resolution gray values for the gratings remains unchanged throughout the scan line. Since every portion of display screen 40 shown in FIGS. 1A–1V consists of either image portion 41 or mask portion 42, only two shades of gray are ever required on one scan line. The shade of gray for one scan line of image portion 41 is known as the SHADE and the shade of gray for one scan line of mask shade 42 is known as the MASK. The high resolution video information is determined line by line instead of pixel by pixel. The 12 bit deep video frame buffer of the prior art can therefore be replaced by a 1 bit deep video frame buffer.

The bars of the grating run parallel to the scan line of the video monitor, thus allowing for use of a slower DAC than is typically used for this purpose. If a system has 512 pixels per scan line, the DAC need only be 1/512th of the speed of a DAC used in a conventional system. This feature provides a major cost and technical advantage.

The brightness at any point of the image on display screen 40 has the resolution of the DAC. That is, with a 12-bit DAC, the brightness resolution of the image is 12 bits even though the frame buffer is only 1-bit deep. Unlike a conventional system, the depth of the frame buffer need not match the resolution of the DAC for proper operation.

A CPU or other processing means used must be fast enough to calculate the high resolution gray values in a timely fashion. Any fast CPU can be used as long as the timing signals are provided either internally or externally. External timing signals can be provided by a commercially available timer/counter peripheral chip, programmable logic devices, gate arrays, or a simple PROM/flip-flop state machine. An inexpensive video coprocessor can also be used. An example of a suitable processor is the Motorola MC68332 which contains a 32 bit CPU and an on-board timer processor unit (TPU). The MC68332, a microcontroller (MCU), is capable of generating most of the video timing signals internally. Some conventional external "glue logic" generates the remainder of timing signals required by the video monitor. Other suitable MCU's include the Hitachi HD6413003.

Figure 4:
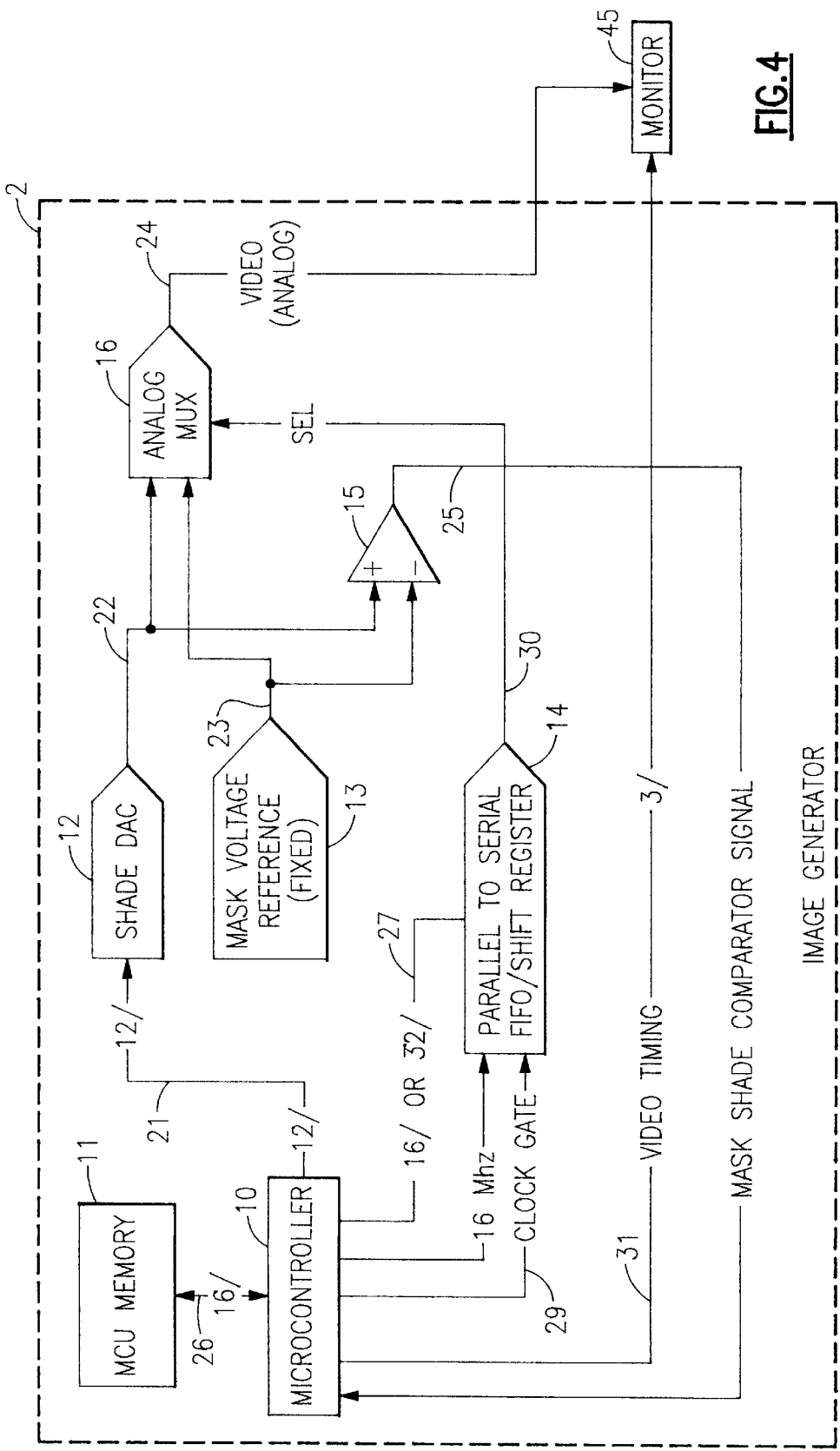
FIG. 4 is a block diagram of an image generator according to an embodiment of the present invention.

Referring to FIG. 4, an image generator 2 includes a microcontroller 10. A specific pattern of MASK and SHADE, generated either externally or internally, resides in an MCU memory 11. Microcontroller 10 receives the pattern from MCU memory 11 via a bus 26, shown here using a 16 bit word, and sends it to a parallel to serial FIFO shift register 14. Based on the desired contrast, a specific gray level is determined and sent via a 12 bit shade signal 21 to a shade DAC (digital to analog converter) 12 which converts 12 bit shade signal 21 to an analog shade signal 22. Shade signal 21 is determined each horizontal retrace period of a video monitor 40. A mask signal 23 is produced by a mask voltage reference 13. Since mask voltage reference 13 is typically not as precise (12 bit) as shade signal 22, shade signal 22 and mask signal 23 are sent to a comparator 15 which outputs a mask shade comparator signal 25. Mask shade comparator signal 25 enables microcontroller 10 to determine the shade DAC 12 output value that equals the mask signal 23 value. This determination is preferably part of a power up calibration procedure so that microcontroller 10 interprets the mask signal 23 value as the mean gray value for generating the gratings. The mask voltage reference level is also known as the mean level and represents the voltage level that is equivalent to a sinusoidal waveform having a contrast of zero. In other words, the mask voltage reference level is a DC offset voltage about which the sinusoidal grating waveform alternates.

Mask voltage reference 13 is optionally another DAC. The calibration procedure described above remains preferable due the differences between individual DAC's. Although a 12-bit DAC has excellent relative tolerances, i.e., one bit to another, the absolute levels of one DAC vary from the absolute levels of another DAC.

Shade signal 22 and mask signal 23 are sent to an analog MUX 16 which outputs an analog video signal 24 to monitor 40. Analog MUX 16 selects either shade signal 22 or mask signal 23 to output as video signal 24 depending on a frame buffer signal 30 output from parallel to serial FIFO shift register 14. Based on the pattern stored in MCU memory 11, microcontroller 10 sends a signal 27 to shift register 14 which simply passes signal 27 on to analog MUX 16 as frame buffer signal 30. Since the frame buffer function resides in memory, frame buffer signal 30 is written as fast as possible without any need for handshaking. A 1 bit video DRAM optionally replaces shift register 14.

Video timing signals 31, preferably produced by an on-board TPU (timing processing unit) in microcontroller 10, provide the basis for horizontal and vertical timing signals to monitor 40. Video blanking signals (not shown) are also produced by the TPU.

The unit can be designed to produce only one pattern-type. Optionally, several modes of operation are possible. In one mode, only one pattern-type is produced. In another mode, a user inputs a desired pattern-type and contrast level to microcontroller 10 through an input means such as, for example, a keyboard. Microcontroller 10 preferably generates a pattern corresponding to the desired pattern-type and stores it in MCU memory 11. During start up calibration, microcontroller 10 receives mask shade comparator signal 25 from comparator 15 to determine the mask and shade levels. Microcontroller 10 preferably generates a 12-bit digital representation of a sinusoidal grating. The amplitude of the these sinusoids is determined by how much contrast is desired on the video monitor: the higher the amplitude, the higher the contrast. Based on the pattern and desired contrast level, microcontroller 10 outputs a shade signal 21 to shade DAC 12 and. DAC 12 thus receives its input directly from microcontroller 10 instead of from a video frame buffer.

Shade signal 22, outputted by DAC 12, and mask signal 23, outputted by mask voltage reference 13, go to analog MUX 16, where one or the other is selected by shift register 14 based on the desired pattern and output as video signal 24 to monitor 45. The frame buffer function of the present invention provides selection between two high resolution analog signals, shade signal 22 and mask signal 23, which can be located anywhere on the monitor screen as defined by a 1 bit frame buffer. Microcontroller 10 produces video timing signal 31 that controls the timing of monitor 45 as it displays video signal 24.

Figure 5:
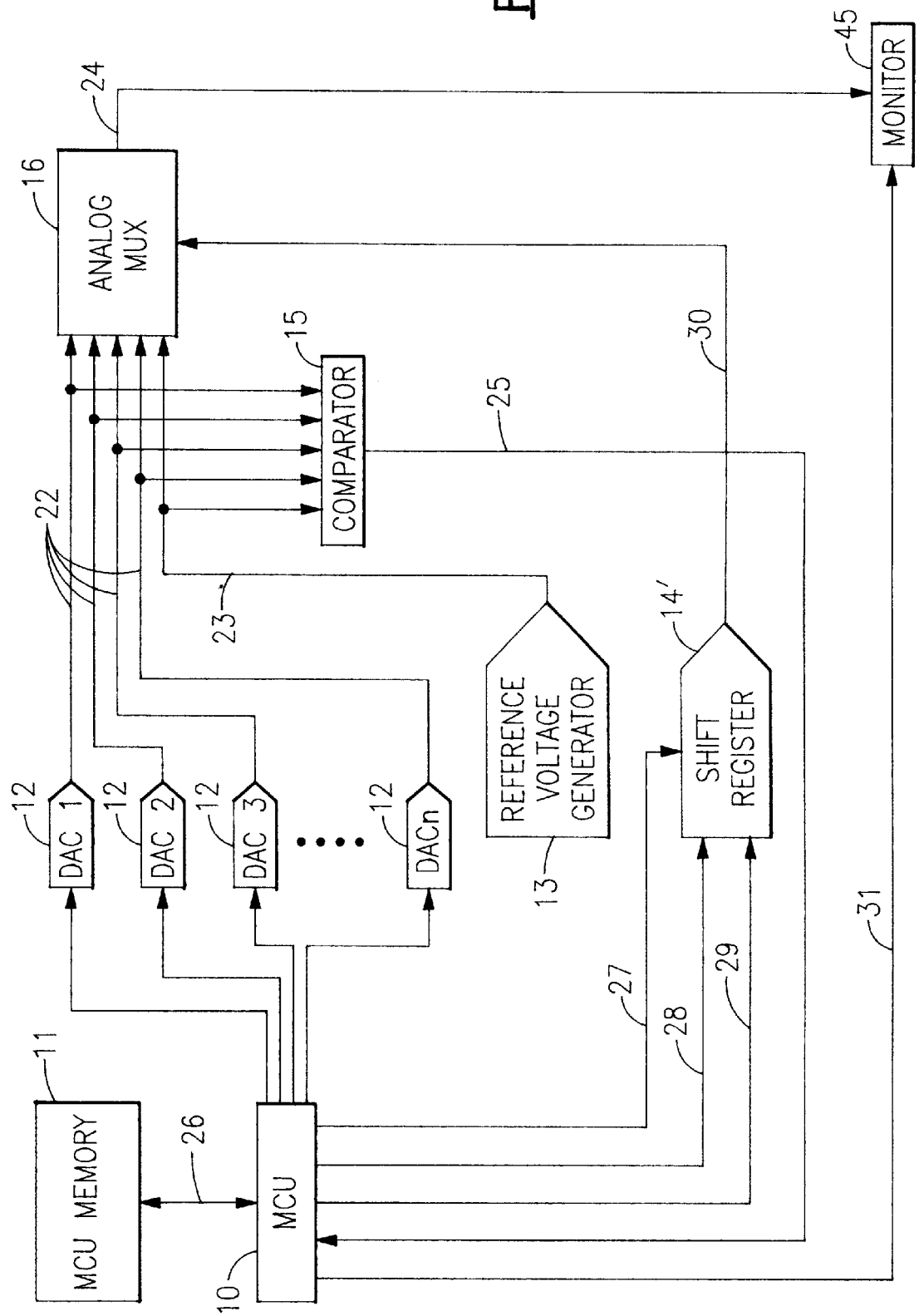
FIG. 5 is a block diagram of an image generator according to an embodiment of the present invention.

Referring to FIG. 5, an embodiment of the present invention provides for more regions by increasing the number of inputs to analog MUX 16. For example, using an n-bit deep shift register 14' instead of 1-bit deep shift register 14 permits using $2^n$-number of DAC's or other voltage sources. Analog MUX 16 must also have $2^n$ inputs. The number of different analog signals, hence different regions on the screen, hence different kinds of bars on the screen is then $2^n$-bits. With n-bit deep shift register 14', the SHADE is defined as the gray value chosen from among the outputs of the $2^n$-number of DAC's by analog MUX 16. The SHADE thus can vary within the scan line.

In certain applications, the SHADE is defined as a different value for every scan line or the MASK can be adjusted.

It is possible to use a digital port in place of DAC 12 and either a digital port or digital constant in place of reference voltage generator 13. The digital outputs then go to a digital MUX with a fast DAC converting the output from the digital MUX to the video input signal.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. In an image generator for use with a video monitor which displays a plurality of scan lines that extend in a scan direction, said image generator being adapted to enable the video monitor to display a line-based image, said image including a pattern comprising a plurality of pattern scan line segments that include pluralities of pixels having brightnesses that are approximately equal and that correspond to respective pattern brightness signal values, and a background comprising a plurality of background scan line segments that include pluralities of pixels having brightnesses that are approximately equal and that correspond to a background brightness signal value, said pattern and background scan line segments being aligned in parallel with one another in a predetermined direction, in combination:

pattern storage means for storing the information necessary to display said image, said pattern storage means including:
   (a.) a one-bit deep frame buffer for storing, on a pixel-by-pixel basis, for each scan line to be displayed on the video monitor, a selection control signal that indicates which pixels are associated with said pattern, and which pixels are associated with said background; and
   (b.) means for storing, on a line-by-line basis, for each scan line to be displayed on the video monitor, the pattern and background brightness signal values that are to be used to display that scan line, said brightness signal values having a brightness resolution of M-bits;
   an analog multiplexer having at least two signal inputs, a control input, and an output for connection to a video input of the video monitor;
   at least two digital to analog converters (DACs) having outputs connected to respective signal inputs of the analog multiplexer;
   a shift register for shiftably applying a one-bit selection control signal to the control input of the analog multiplexer;
   processing means, responsive to said pattern storage means, for:
   (a.) supplying to said DACs, prior to displaying each scan line of the video monitor, the pattern and background brightness signal values that are associated with that scan line; and
   (b.) supplying to said shift register, prior to displaying each scan line of the video monitor, the selection control signal that is associated with that scan line; and
   means for clocking said shift register to display said image;
   wherein the scan direction of the video monitor and said predetermined direction are parallel to one another, whereby the video monitor is able to display scan line segments having a brightness resolution of M-bits, even though said frame buffer is a one-bit deep frame buffer.

2. An image generator as set forth in claim 1 in which the video monitor uses timing signals that establish a frame rate, a line rate and a dot rate, in which said plurality of DACs are clocked at said line rate, and in which said shift register is clocked at said dot rate, whereby said DACs may have a digital to analog conversion rate which is low in relation to said dot rate.

3. In an image generator for use with a video monitor which displays a plurality of scan lines that extend in a scan direction, said image generator being adapted to cause the video monitor to display a line-based image, said image including a pattern comprising a plurality of pattern scan line segments, at least one of which includes two or more component scan line segments, said scan line segments and component scan line segments each including pluralities of pixels having brightnesses that are approximately equal and that correspond to respective pattern brightness signal values, and a background comprising a plurality of background scan line segments each including pluralities of pixels having brightnesses that are approximately equal and that correspond to a background brightness signal value, said pattern and background scan line segments being aligned in parallel with one another in a predetermined direction, in combination:

pattern storage means for storing the information necessary to display said image, said pattern storage means including:

(a.) an N-bit deep frame buffer for storing, on a pixel-by-pixel basis, for each scan line to be displayed on the video monitor, an up to N-bit selection control signal that indicates which pixels are associated with the scan line and component scan line segments of said pattern, and which pixels are associated with said background; and (b.) means for storing, on a line-by-line basis, for each scan line to be displayed on the video monitor, the pattern and background brightness signal values that are to be used to display that scan line, said brightness signal values having a resolution of M-bits, M being large in relation to N;

an analog multiplexer having up to $2^N$ signal inputs, up to N control inputs, and an output for connection to a video input of the video monitor;

up to N digital to analog converters (DACs) having outputs connected to respective signal inputs of the analog multiplexer;

a shift register for shiftably applying an up to N-bit selection control signal to the control inputs of the analog multiplexer;

processing means, responsive to said pattern storage means, for:

(a.) supplying to said DACs, prior to displaying each scan line of the video monitor, the pattern and background brightness signal values that are associated with that scan line; and (b.) supplying to said shift register, prior to displaying each scan line of the video monitor, the selection control signal that is associated with that scan line; and means for clocking said shift register to display said image;

wherein the scan direction of the video monitor and said predetermined direction are parallel to one another, whereby the video monitor is able to display scan line segments and component scan line segments having brightness resolutions of M-bits, even though said frame buffer is an N-bit deep frame buffer.

4. An image generator as set forth in claim 3 in which the number of component scan line segments, in each scan line segment that includes two or more component scan line segments, is small in relation to the number of pixels associated with those component scan line segments.

5. An image generator as set forth in claim 3 in which the video monitor uses timing signals that establish a frame rate, a line rate and a dot rate, in which said up to N DACs are clocked at said line rate, and in which said shift register is clocked at said dot rate, whereby said DACs may have a digital to analog conversion rate which is low in relation to said dot rate.

6. In an image generator for use with the video monitor of an instrument that detects abnormalities in human beings by controllably displaying a brightness modulated grating pattern of the type used in tests based on at least one of contrast sensitivity and a frequency doubled illusion effect, said video monitor having a display screen that displays a plurality of scan lines that extend in a scan direction, said grating pattern comprising a plurality of scan line segments each including pluralities of pixels having brightnesses that correspond to respective pattern brightness signal values, and a background comprising a plurality of background scan line segments that include pluralities of pixels having brightnesses that correspond to a background brightness signal value, said pattern and background scan line segments being aligned in parallel with one another in a predetermined direction, in combination:

pattern storage means for storing the information necessary to display said grating pattern and said background, said pattern storage means including:

(a.) a one-bit deep frame buffer for storing, on a pixel-by-pixel basis, for each scan line displayed on the video monitor, a selection control signal that indicates which pixels are associated with said grating pattern, and which pixels are associated with said background; and (b.) means for storing, on a line-by-line basis, for each scan line displayed on the video monitor, the pattern and background brightness signal values that are to be used to display that scan line, said brightness signal values having a brightness resolution of M-bits;

an analog multiplexer having at least two signal inputs, a control input, and an output for connection to a video input of the video monitor;

at least two digital to analog converters (DACs) having outputs connected to respective signal inputs of the analog multiplexer;

a shift register for shiftably applying said selection control signal to the control input of the analog multiplexer;

processing means, responsive to said pattern storage means, for:

(a.) supplying to said DACs, prior to displaying each scan line of the video monitor, the pattern and background brightness signal values that are associated with that scan line; and (b.) supplying to said shift register, prior to displaying each scan line of the video monitor, the selection control signal that is associated with that scan line; and means for clocking said shift register to display said grating pattern and said background;

wherein the scan direction of the video monitor and said predetermined direction are parallel to one another, whereby the video monitor is able to display scan line segments having a brightness resolution of M-bits, even though said frame buffer is a one-bit deep frame buffer.

7. An image generator as set forth in claim 6 in which the video monitor uses timing signals that establish a frame rate, a line rate and a dot rate, in which said plurality of DACs are clocked at said line rate, and in which said shift register is clocked at said dot rate, whereby said plurality of DACs may have digital to analog conversion rates which are low in relation to said dot rate.

8. An image generator according to claim 7 in which the grating pattern is characterized by a contrast dependent upon the relationship between the maximum and minimum brightnesses of the scan line segments comprising that grating pattern, and in which said processing means is programmed to allow a user to adjust said brightness signal values to vary the contrast with which the grating pattern is displayed.

9. An image generator according to claim 6 in which the grating pattern is characterized by a contrast dependent upon the relationship between the maximum and minimum brightnesses of the scan line segments comprising that grating pattern, and in which said processing means is programmed to allow a user to vary the contrast with which the grating pattern is displayed.

10. An image generator according to claim 6 in which said processing means is adapted to periodically change the brightness signal values associated with the scan line segments of the grating pattern between two alternative values, thereby causing the video monitor to appear to display said grating pattern in two alternative phase positions that are suitable for producing a frequency doubled illusion effect.

11. In an image generator for use with the video monitor of an instrument that detects abnormalities in human beings by controllably displaying a brightness modulated grating pattern of the type used in tests based on at least one of contrast sensitivity and a frequency doubled illusion effect, said video monitor having a display screen that displays a plurality of scan lines that extend in a scan direction, said grating pattern comprising a plurality of pattern scan line segments, at least one of which includes two or more component scan line segments, said scan line segments and component scan line segments each including pluralities of pixels having brightnesses that correspond to respective pattern brightness signal values, and a background comprising a plurality of background scan line segments each including pluralities of pixels having a brightnesses that correspond to a background brightness signal value, said pattern and background scan line segments being aligned in parallel with one another in a predetermined direction, in combination:

pattern storage means for storing the information necessary to display said grating pattern and said background, said pattern storage means including:
(a.) an N-bit deep frame buffer for storing, on a pixel-by-pixel basis, for each scan line displayed on the video monitor, a selection control signal that indicates which pixels are associated with the scan line and component scan line segments of the grating pattern, and which pixels are associated with said background; and
(b.) means for storing, on a line-by-line basis, for each scan line displayed on the video monitor, the pattern and background brightness signal values that are to be used to display that scan line, at least two of said brightness signal values having a resolution of M-bits, M being large in relation to N;
an analog multiplexer having up to $2^N$ signal inputs, up to N control inputs, and an output for connection to a video input of the video monitor;
up to N digital to analog converters (DACs) having outputs connected to respective signal inputs of the analog multiplexer;

a shift register for shiftably applying said selection control signal to the control inputs of the analog multiplexer;
processing means, responsive to said pattern storage means, for:
(a.) supplying to said DACs, prior to displaying each scan line of the video monitor, the pattern and background brightness signal values that are associated with that scan line; and
(b.) supplying to said shift register, prior to displaying each scan line of the video monitor, the selection control signal that is associated with that scan line; and
means for clocking said shift register to display said grating pattern and said background;
wherein the scan direction of the video monitor and said predetermined direction are parallel to one another, whereby the video monitor is able to display scan line segments and component scan line segments having brightness resolutions of M-bits, even though said frame buffer is an N-bit deep frame buffer.

12. An image generator as set forth in claim 11 in which the number of component scan line segments, in each scan line segment that includes two or more component scan line segments, is small in relation to the number of pixels associated with those component scan line segments.

13. An image generator as set forth in claim 11 in which the video monitor uses timing signals that establish a frame rate, a line rate and a dot rate, in which said up to N DACs are clocked at said line rate, and in which said shift register is clocked at said dot rate, whereby said up to N DACs may have a digital to analog conversion rate which is low in relation to said dot rate.

14. An image generator according to claim 13 in which the grating pattern is characterized by a contrast dependent upon the relationship between the maximum and minimum brightnesses of the scan line segments comprising the grating pattern, and in which said processing means is programmed to allow a user to vary the contrast with which the grating pattern is displayed.

15. An image generator according to claim 13 in which the grating pattern is characterized by a contrast dependent upon the relationship between the maximum and minimum brightnesses of the scan line segments comprising the grating pattern, and in which said processing means is programmed to allow a user to vary the contrast with which the grating pattern is displayed.

16. An image generator according to claim 13 in which said processing means is adapted to periodically change the brightness signal values associated with the scan line segments of the grating pattern, thereby causing the video monitor to appear to display the grating pattern in two alternative phase positions that are suitable for producing a frequency doubled illusion effect.

* * * * *